(12) United States Patent
Nadim et al.

(10) Patent No.: US 11,172,925 B2
(45) Date of Patent: Nov. 16, 2021

(54) SUTURE PASSER WITH CLAMPING TIP

(71) Applicant: Ring Orthopedics, Inc., Tampa, FL (US)

(72) Inventors: Yasser Abdelsalam Nadim, Somerset, KY (US); Lance Fagan, Bartow, FL (US)

(73) Assignee: Ring Orthopedics, Inc., Tampa, FL (US)

( * ) Notice: Subject to any disclaimer, the term of this patent is extended or adjusted under 35 U.S.C. 154(b) by 337 days.

(21) Appl. No.: 16/459,686

(22) Filed: Jul. 2, 2019

(65) Prior Publication Data

US 2019/0336125 A1  Nov. 7, 2019

Related U.S. Application Data

(63) Continuation-in-part of application No. 16/167,761, filed on Oct. 23, 2018, now Pat. No. 10,368,858.

(60) Provisional application No. 62/622,057, filed on Jan. 25, 2018.

(51) Int. Cl.
  *A61B 17/04* (2006.01)
  *A61B 17/06* (2006.01)

(52) U.S. Cl.
  CPC ...... *A61B 17/0487* (2013.01); *A61B 17/0469* (2013.01); *A61B 17/0482* (2013.01); *A61B 2017/061* (2013.01)

(58) Field of Classification Search
  CPC ........... A61B 17/0469; A61B 17/0482; A61B 17/0483; A61B 17/0485; A61B 17/0487; A61B 17/062; A61B 17/12013; A61B 17/29; A61B 2017/0488; A61B 2017/061
  See application file for complete search history.

(56) References Cited

U.S. PATENT DOCUMENTS

| | | | |
|---|---|---|---|
| 5,222,973 A * | 6/1993 | Sharpe | A61B 17/29 294/100 |
| 5,318,589 A * | 6/1994 | Lichtman | A61B 17/29 600/564 |
| 5,665,096 A * | 9/1997 | Yoon | A61B 17/0469 606/139 |
| 5,817,112 A | 10/1998 | Christoudias | |
| 8,709,022 B2 | 4/2014 | Stone | |
| 2013/0218173 A1 | 8/2013 | Weisel | |
| 2015/0282806 A1 | 10/2015 | Jorgensen | |

* cited by examiner

*Primary Examiner* — Robert A Lynch
(74) *Attorney, Agent, or Firm* — Larson & Larson, P.A.; Justin P. Miller; Frank Liebnow (57) ABSTRACT

The suture passer includes a body, from which two mechanisms protrude: a hollow needle through which a suture is guided, the suture exiting at the surgical site; and a sliding hollow tube with a distal opening, with a pincer/clamp/jaws held within the sliding hollow tube. The two primary parts of the suture passer are the hollow needle and the retrieval member.

11 Claims, 8 Drawing Sheets

SUTURE PASSER WITH CLAMPING TIP

CROSS-REFERENCE TO RELATED APPLICATION

This application is a continuation-in-part of U.S. patent Ser. No. 16/167,761, filed Oct. 23, 2018, titled Suture Passer, which in turn claimed priority to U.S. Pat. App. Ser. No. 62/622,057, filed Jan. 25, 2018, titled Novel suture passing and retrieving device to pass and retrieve suture and other filamentary material in arthroscopic surgery.

FIELD

This invention relates to the field of surgical instruments and more particularly to a device for gripping sutures during arthroscopic surgery.

BACKGROUND

Arthroscopic surgery is a surgical procedure performed on a joint of the body, the instruments working through a small slit in the skin.

Patients who receive arthroscopic surgery, as compared to traditional surgery with its large incisions, experience decreased recovery time and a reduced number of complications.

But the limitations of arthroscopic surgery imposed on the surgeon, including confined access created by small incisions and decreased working volume, create issues for surgeons. For example, a surgeon's hands cannot directly reach into the surgical site to retrieve a suture or tie a knot. The result is that the complexity, from the perspective of the surgeon, is increased.

An additional layer of complexity is added by the conditions under which the surgery is performed. Specifically, the constant flow of fluid that passes through the surgical site in order to remove debris and blood. As result of this constant flushing action, any suture that is not able to be held in place is washed downstream, making retrieval difficult. Thus, suture control in arthroscopic is a complex issue as compared to conventional open surgery.

Given that conventional needle and suture thread cannot access the surgical site, and that suture control is a critical issue during surgery, an alternative to traditional tools is needed.

What is needed is a simple, reliable device that allows suture to be passed to the surgical site, and then manipulated in-place, for use within surgical sites with limited access.

SUMMARY

The suture passer includes a body, from which two mechanisms protrude: a hollow needle through which a suture is guided, the suture exiting at the surgical site; and a sliding hollow tube with a distal opening, with a pincer/clamp/jaws held within the sliding hollow tube.

The two primary parts of the suture passer are the hollow needle and the retrieval member.

The hollow needle caries the suture to the desired location. An inserted suture follows the interior of the hollow needle, exiting into the surgical site at the suture exit. Prior to the exit is preferably located a curve. The curve shifts the direction of the hollow needle, and correspondingly the suture, to direct the suture toward the clamping location of the retrieval member. This curve is not required, as in alternative embodiments the sliding hollow tube of the retrieval member is straight.

The hollow needle optionally includes a cutting tip to help the tip pass through tissue.

The hollow needle of the suture passer is fixed with respect to the body and handle. Thus, the surgeon may manipulate the handle in order to control the hollow needle. In alternative embodiments the hollow needle has multiple fixed positions with respect to the handle to provide the surgeon with placement options.

The retrieval member has multiple positions to move the pincer toward and away from the suture exit of the hollow needle.

The process of passing and grasping a suture is as follows.
The suture passer starts in a position with the jaws retracted and closed.
A suture is pushed through the suture passage, and into the suture entrance of the hollow needle. The suture exits the hollow needle at the suture exit.
The tube actuator that controls the hollow tube is then pulled back, exposing the jaws, which spring open.
The jaw actuator and tube actuator are moved forward together, in a path parallel to the hollow needle, placing the open jaws around the suture.
The tube actuator is then slid forward, toward the jaw actuator, enclosing the jaws with the hollow tube. Surrounding the jaws with the hollow tube acts to close the jaws, the jaws gripping the suture.
The jaw actuator and tube actuator are then moved backward together, retrieving the suture.

The jaws have a bore at the base of their arms, and relief cuts on the adjacent sides. These areas of missing material promote flexibility to create natural, or living, hinge points.

The jaws will be manufactured in a manner where the natural jaw position is open, thus encouraging the jaws to open when not surrounded by the hollow tube.

The retrieval member moves along a path parallel to the position of the hollow needle. Thus, when the jaws of the retrieval member are opened and extended, the jaws are specifically positioned with respect to the exit of the hollow needle to grasp an exiting suture. By using rigid materials, the jaws will not appreciably flex or deviate from their path of motion, thus the surgeon can depend on the jaws being ready to grasp the suture.

The flow of fluid through the surgical site will not affect the ability of the surgeon to predict the location of the exiting suture.

The hollow tube and retrieval member are controlled by a split actuator that slides within a slot along the handle.

The jaw actuator moves a connecting rod within the hollow tube, moving the jaws in and out of the hollow tube.

The hollow tube actuator moves the hollow tube in and out of the body, a tube channel within the body guiding the motion of the hollow tube of the retrieval member. Thus, the retrieval member is maintained in a parallel relationship with respect to the hollow needle.

The jaw actuator and hollow tube actuator each have associated pins. The jaw actuator pin moves within a slot cut into the hollow tube. The slot limits the range of motion of the jaw actuator with respect to the hollow tube, thereby defining a range of motion for the jaws with respect to the tip of the hollow tube.

Regarding materials, the body of the suture passer is preferably plastic, but may be formed from other materials such as metal.

The hollow needle is preferably formed from surgical stainless steel, such as 316, 420, or 440 stainless steel. But other materials are acceptable.

The preferred material for the connecting rod and jaws is a precipitation-hardened grade of stainless steel often used in manufacture of surgical instruments (e.g. 17-4PH stainless heat treated to material condition H900).

Discussion now turns to the drawings.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
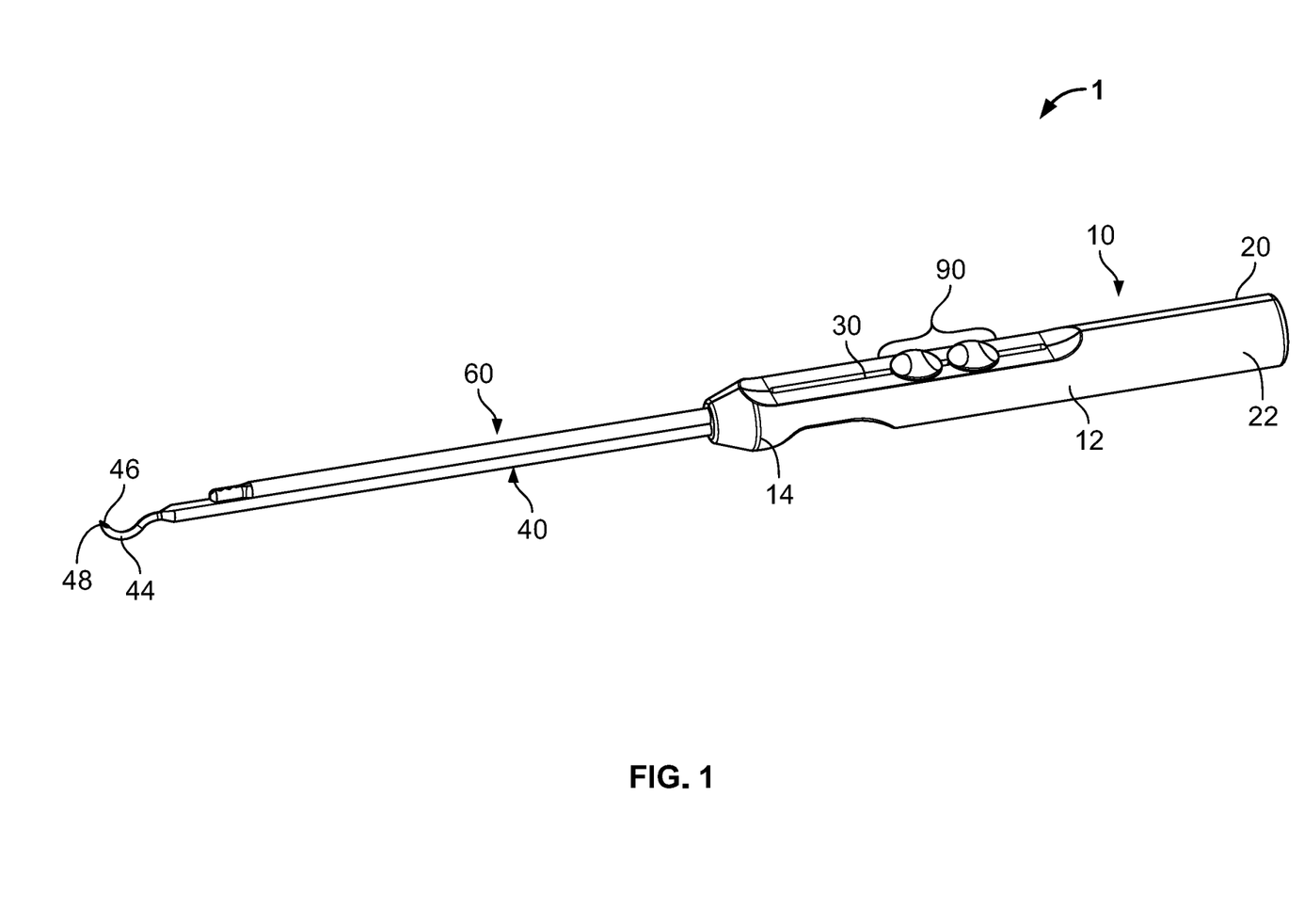
FIG. 1 illustrates a first isometric view of the suture passer with clamping tip.

Referring to FIG. 1, a first isometric view of the suture passer with clamping tip is shown.

The primary components are the body 10, hollow needle 40 and retrieval member 60. The body 10 is split into a first half 20 and a second half 22. The body includes grip 12 and guard 14.

A slot 30 at the top of the body 10 guides the movement of a split actuator 90 that actuates the parts forming the retrieval member 60.

The hollow needle 40 changes direction at a curved guide 44, terminated at the suture exit 46 with optional cutting tip 48.

Figure 2:
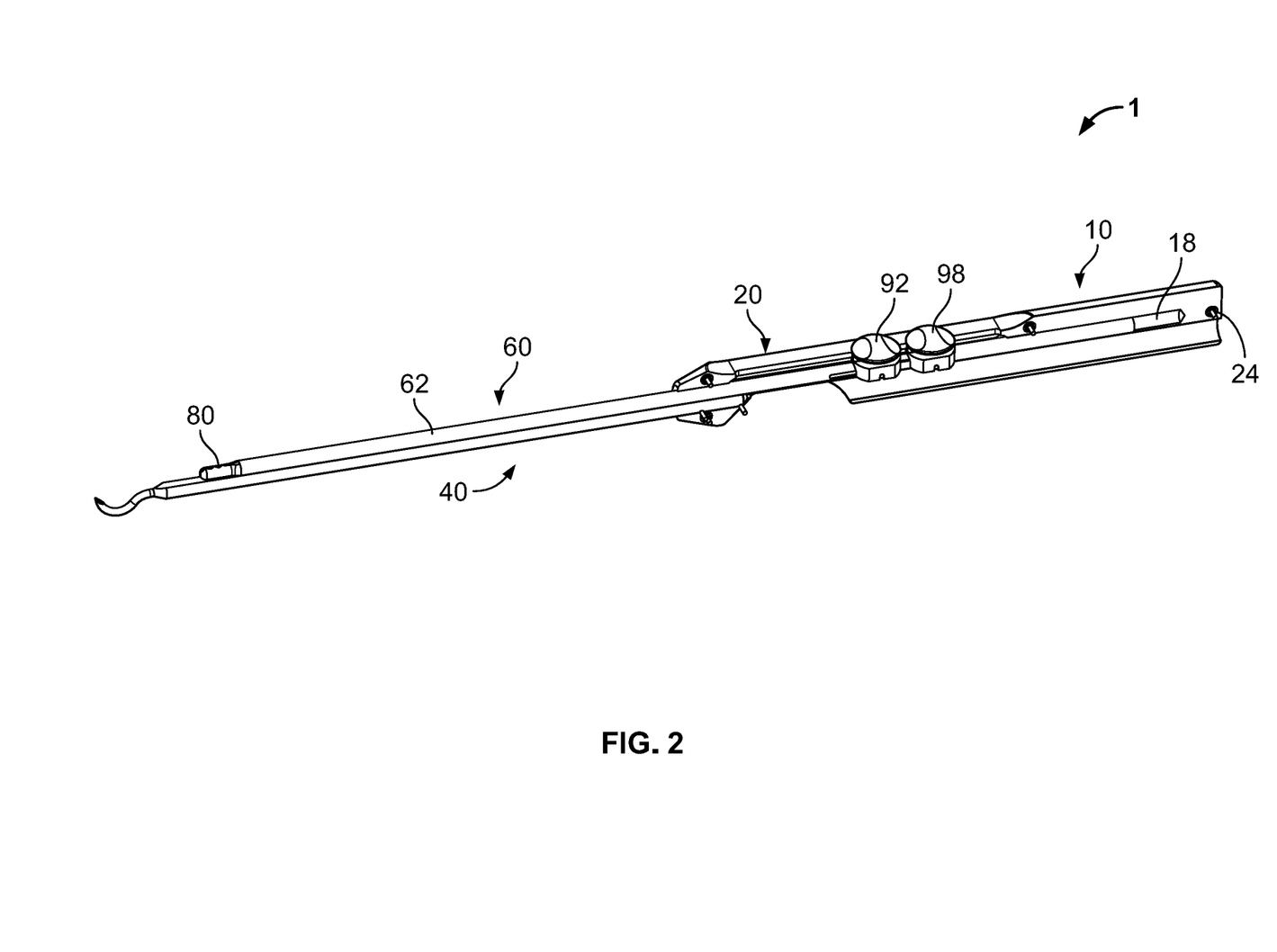
FIG. 2 illustrates a second isometric view with the interior of the body exposed of the suture passer with clamping tip.

Referring to FIG. 2, a second isometric view with the interior of the body exposed of the suture passer with clamping tip is shown.

The suture passer 1 is shown with first half 20 of the body 10 shown, and second half 22 hidden (see FIG. 1). Pins 24 align the first half 20 and second half 22.

Also shown are the sliding hollow tube 62 and jaws 80 of retrieval member 60. The sliding hollow tube 62 moves with the tube channel 18 of the body 10.

Figure 3:
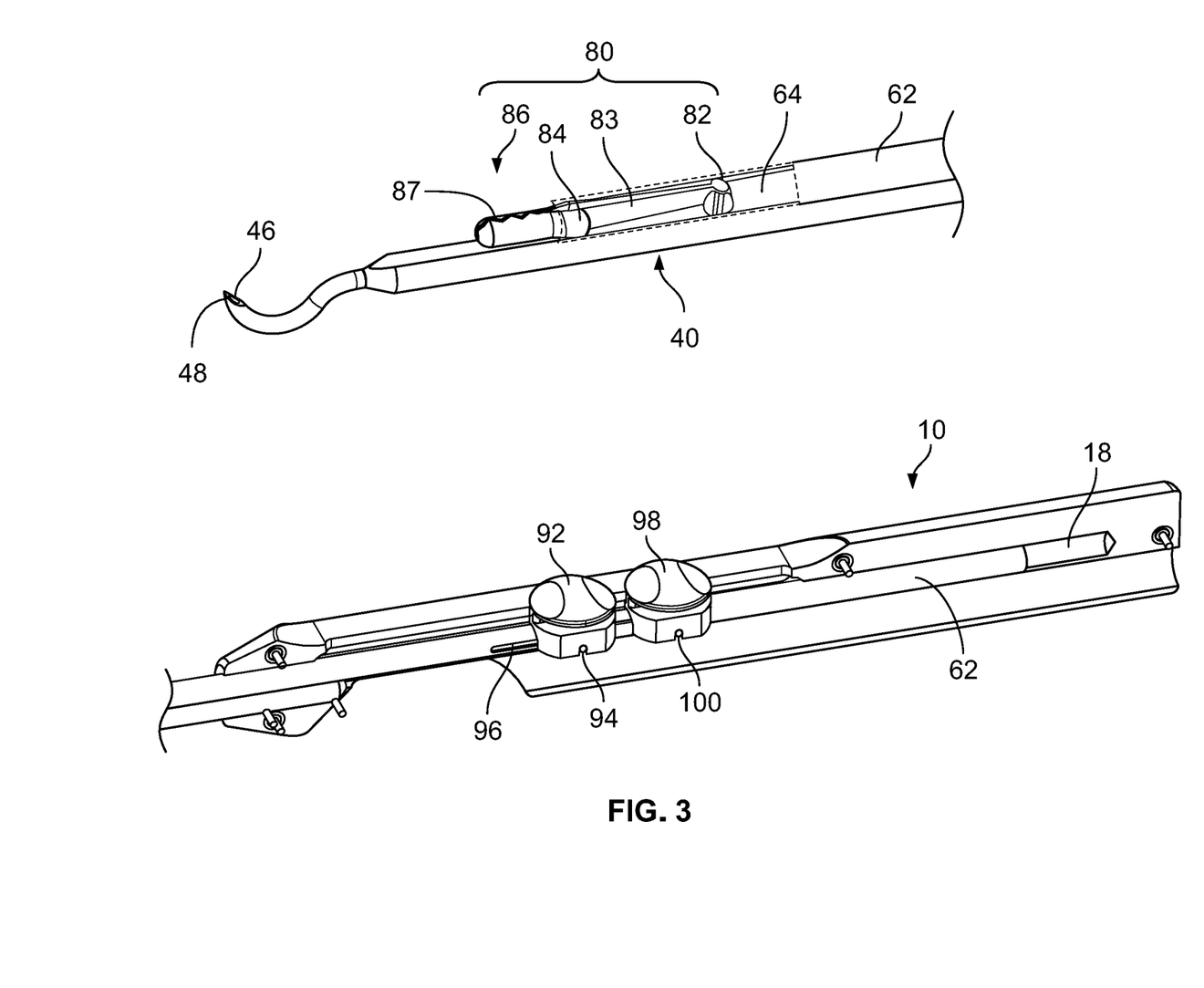
FIG. 3 illustrates an isometric view with the jaws in a retracted and closed position before insertion of a suture.

The jaws 62 terminate at connecting rod 64 (see FIG. 3, the connecting rod 64 sliding within the hollow tube 62.

The split actuator 90 (see FIG. 1) is shown as jaw actuator 92 and tube actuator 98.

Referring to FIG. 3, an isometric view with the jaws in a retracted and closed position before insertion of a suture into the suture passer with clamping tip is shown.

The jaws 80 are visible. The transition from the connecting rod 64 begins with a primary hinge 82, connected to arms 83, which each have a secondary hinge 84. The arms 83 end in the clamping tip 86 that optionally includes teeth 87.

Turning to the body 10, the jaw actuator 92 moves jaw pin 94, jaw pin 94 passing through connecting rod 64. Thus, motion of jaw actuator 92 moves connecting rod 64 and jaws 80.

The motion of jaw pin 94 is limited by the jaw pin slot 96 within the sliding hollow tube 62. The jaw pin slot 96 thus limits the movement of the jaws 80 with respect to the sliding hollow tube 62, thus preventing the jaws 80 from sliding too far in or out of the sliding hollow tube 62.

The tube actuator 98 corresponding has tube pin 100, tube pin 100 controlling the position of sliding hollow tube 62.

Figure 4:
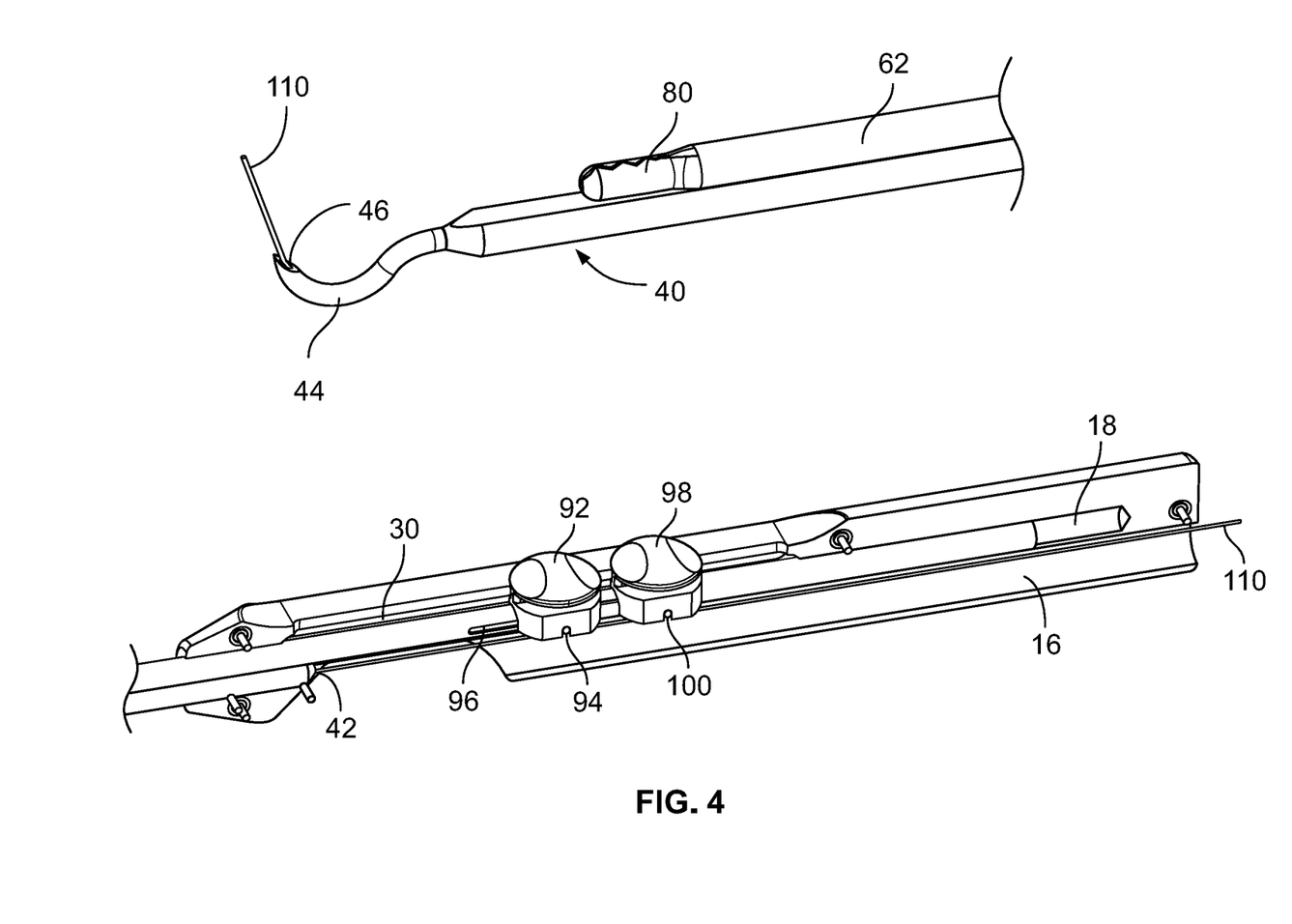
FIG. 4 illustrates an isometric view with the jaws in a retracted and closed position after insertion of a suture.

Referring to FIG. 4, an isometric view with the jaws in a retracted and closed position of the suture passer with clamping tip is shown.

A suture 110 has been introduced to the suture passer 1. The suture 110 passes through the suture passage 16, into the suture entrance 42, through the hollow needle 40, and out the suture exit 46.

Figure 5:
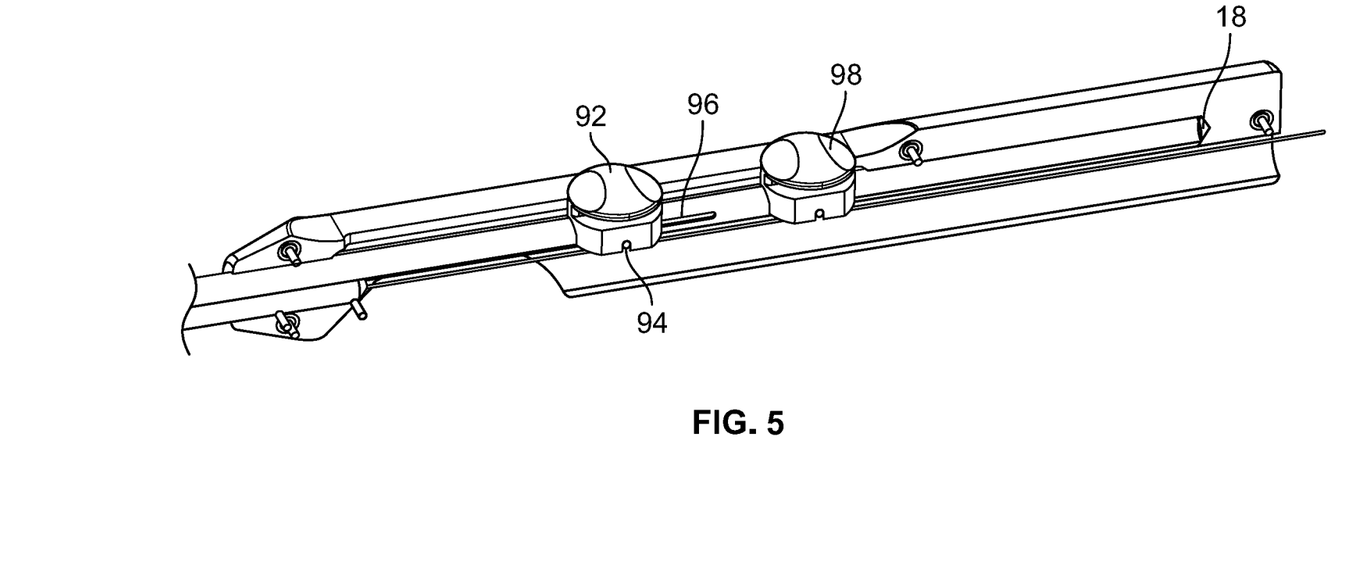
FIG. 5 illustrates an isometric view with the jaws in a retracted and open position.

Referring to FIG. 5, an isometric view with the jaws in a retracted and open position of the suture passer with clamping tip is shown.

The jaw actuator 92 and jaw pin 94 have moved forward within the jaw pin slot 96, fully extending the jaws 80. The jaws 80 naturally pop open after leaving the confinement of the sliding hollow tube 62.

Figure 6:
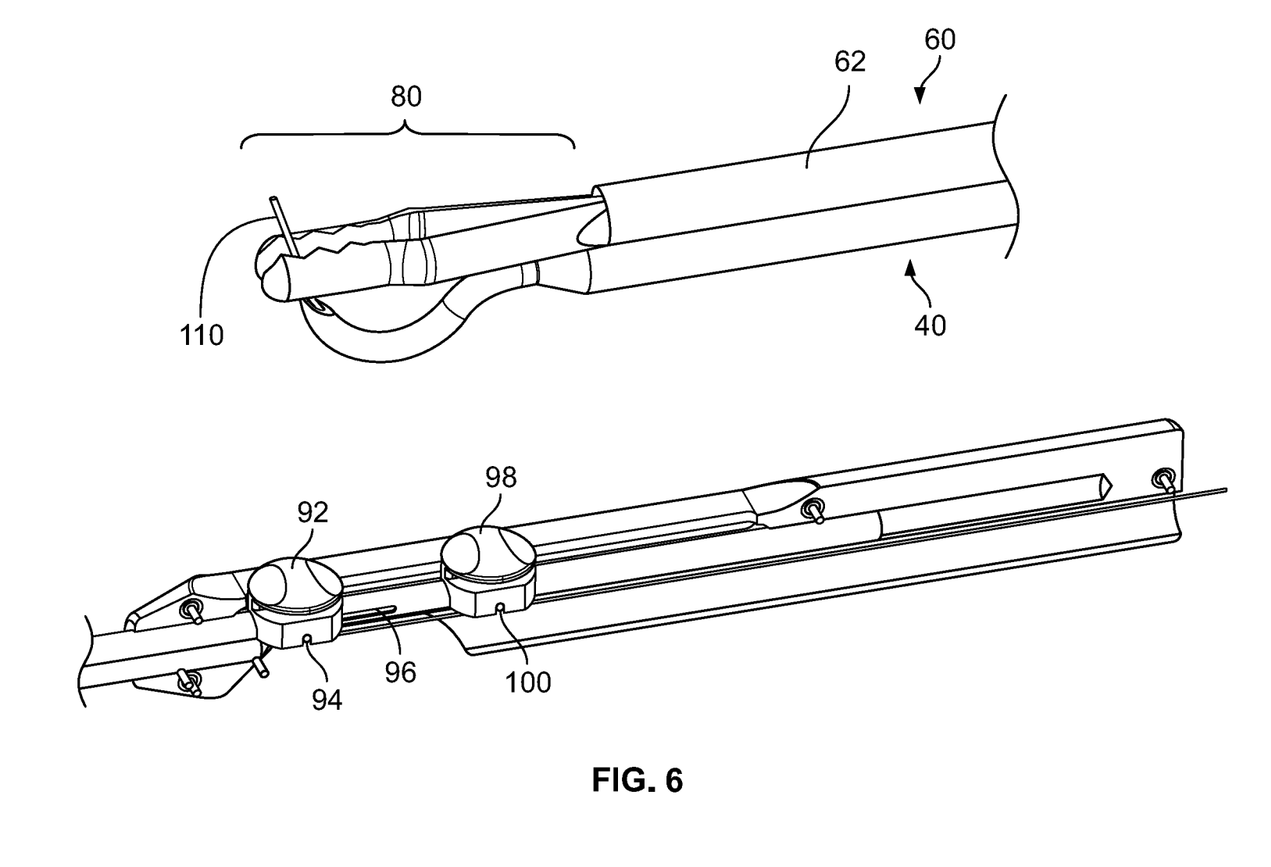
FIG. 6 illustrates an isometric view with the jaws in an extended and open position.

Referring to FIG. 6, an isometric view with the jaws in an extended and open position of the suture passer with clamping tip is shown.

The jaw actuator 92 and tube actuator 98 have moved together, sliding the retrieval member 60 outward with respect to the hollow needle 40. The clamping tip 86 of the jaws 80 now surrounds the suture 110, preparing to grasp the suture 110 and carry it back.

Figure 7:
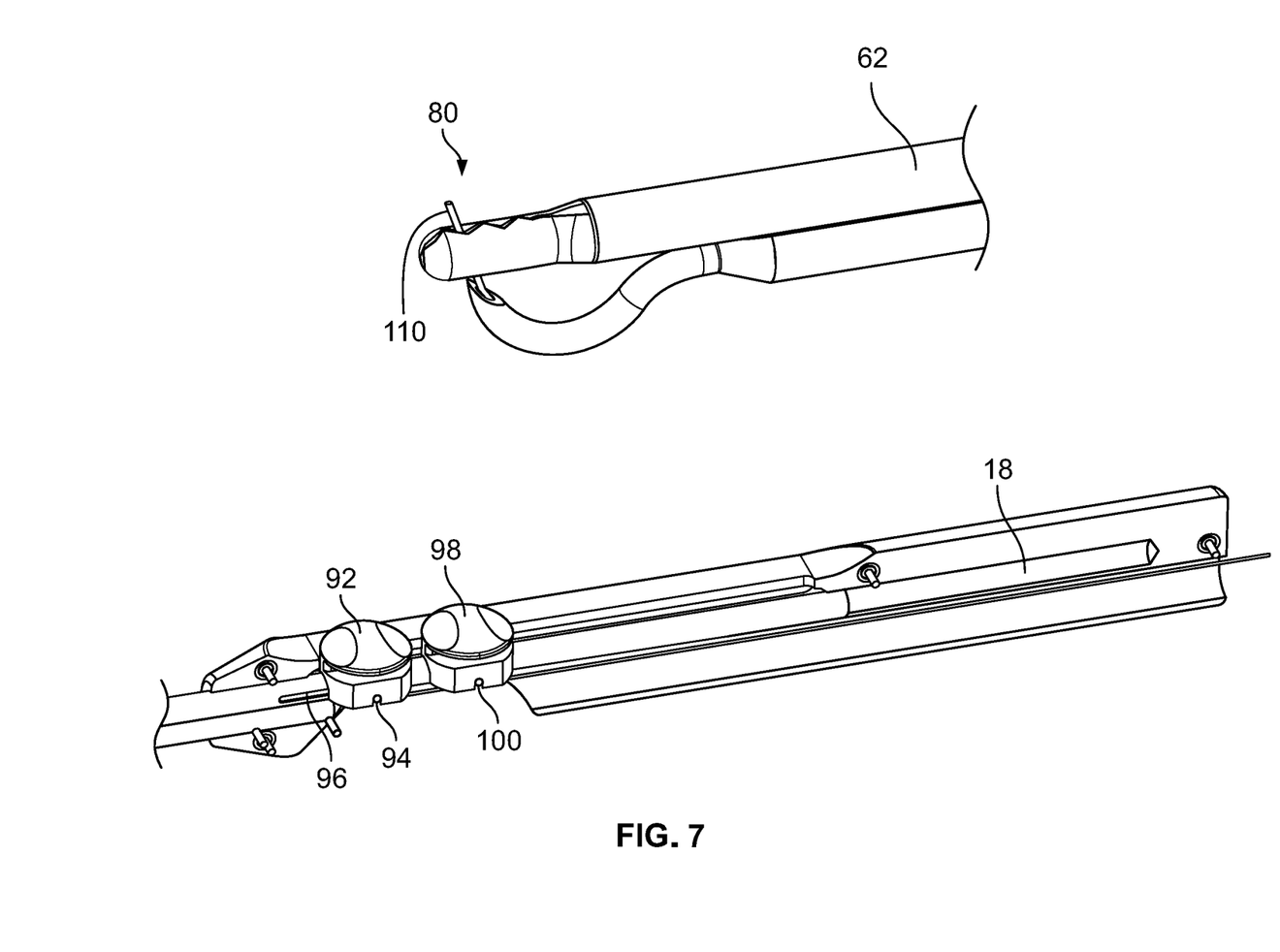
FIG. 7 illustrates an isometric view with the jaws in an extended and closed position.

Referring to FIG. 7, an isometric view with the jaws in an extended and closed position of the suture passer with clamping tip is shown.

The tube actuator 98 has moved outward, pushing the sliding hollow tube 62 over arms 83 of the jaws 80.

The result is the clamping tip 86 of the jaws 80 presses against and gripping the suture 110.

Figure 8:
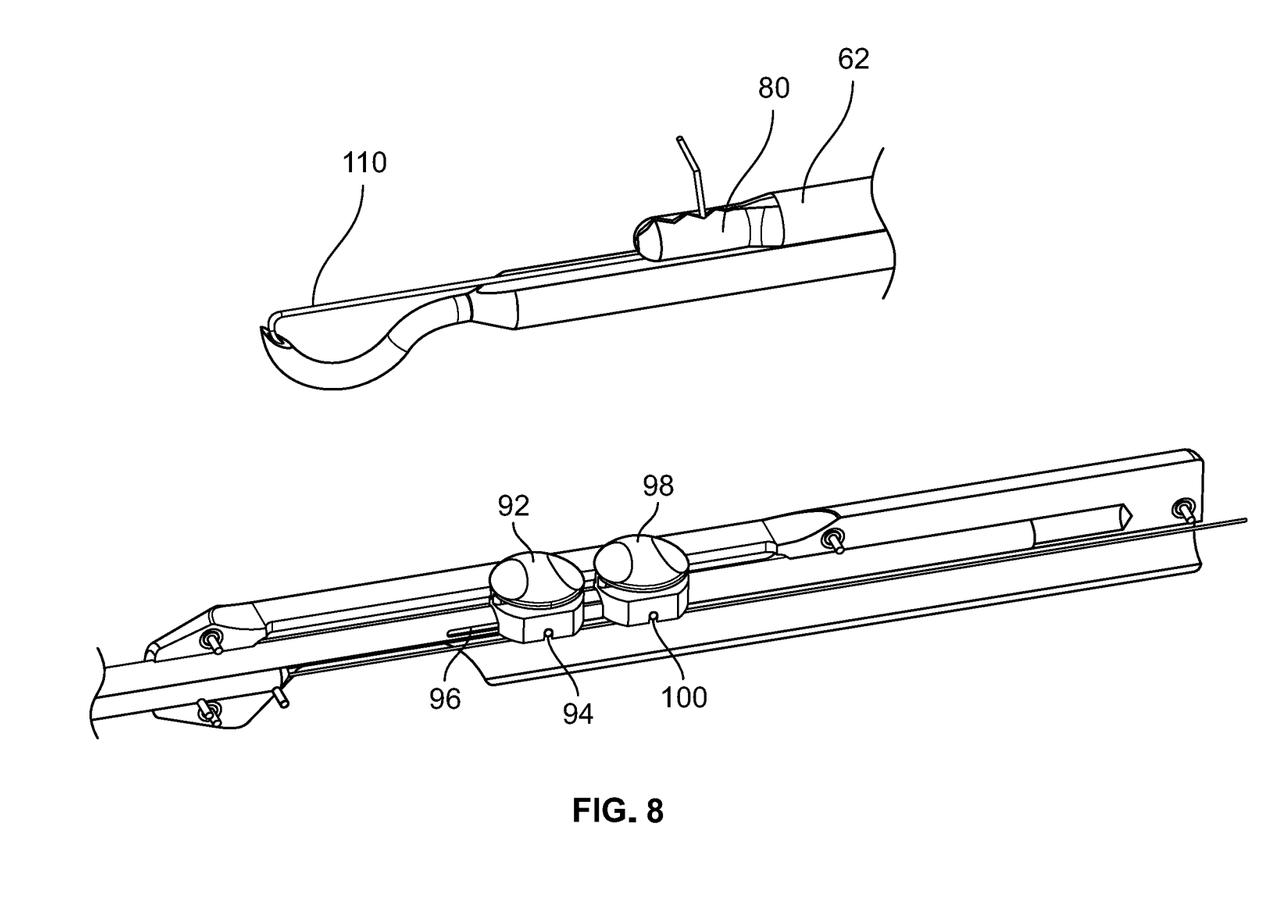
FIG. 8 illustrates an isometric view with the jaws in an retracted and closed position.

Referring to FIG. 8, an isometric view with the jaws in a retracted and closed position is shown. The jaw actuator 92 and tube actuator 98 have moved together, toward the body. The resulting motion brings the retrieval member 60 inward with respect to the hollow needle 40, retrieving the suture 110.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A suture passer for arthroscopic surgery comprising:
a body;
a hollow needle affixed to the body;
a retrieval mechanism including:
   a hollow tube;
      the hollow tube sliding with respect to the body;
      the hollow tube having a proximal end and a distal end;
   a connecting rod;
      the connecting rod sliding within the hollow tube;
   clamping jaws;
      the clamping jaws at a first end of the connecting rod;
      the clamping jaws closed when partially surrounded by the hollow tube;
      the clamping jaws open when outside the hollow tube;
a jaw actuator;
   inward and outward motion of the jaw actuator moving the connecting rod toward and away from the body;
a hollow tube actuator;
   inward and outward motion of the hollow tube actuator moving the hollow tube toward and away from the body;
a jaw pin that connects the jaw actuator to the connecting rod; and
a tube pin that connects the hollow tube actuator to the hollow tube;
whereby the hollow tube acts to close the clamping jaws by partially surrounding the clamping jaws;
whereby a suture may pass through the hollow needle to exit at a surgical site, where the clamping jaws may grasp and retrieve the suture.

2. The suture passer of claim 1, further comprising:
a jaw pin slot within the hollow tube;
   the jaw pin free to slide within the jaw pin slot;
   the jaw pin slot defining a range of motion of the clamping jaws with respect to the connecting rod, the limits of the range of motion including the clamping jaws open, and the jaws closed but partially exposed to avoid interference with the suture.

3. The suture passer of claim 2, wherein the hollow needle further comprises:
a curved guide;
   the curved guide altering the path of the suture from parallel to the retrieval mechanism, to causing the suture to exit toward the clamping jaws.

4. The suture passer of claim 1, wherein the clamping jaws are formed from:
a primary hinge between the clamping jaws and the connecting rod;
two arms extending from the primary hinge, each arm of the two arms including a secondary hinge; and
a clamping tip formed by tips of the two arms.

5. A suture passer comprising:
a hollow needle;
a hollow tube;
a connecting rod;
a pair of jaws;
   the pair of jaws attached via a hinge to an end of the connecting rod;
   the pair of jaws, in the absence of an outside force, moving to an open and separated position;
a body;
   the hollow needle affixed to the body;
   the hollow tube sliding with respect to the body;
   outward motion of the hollow tube, with respect to the connecting rod, surrounding the jaws and causing the jaws to close;
   inward motion of the hollow tube, with respect to the connecting rod, uncovering the jaws and allowing the jaws to open;
a jaw actuator;
   inward and outward motion of the jaw actuator moving the connecting rod toward and away from the body;
a hollow tube actuator;
   inward and outward motion of the hollow tube actuator moving the hollow tube toward and away from the body;
a jaw pin that connects the jaw actuator to the connecting rod; and
a tube pin that connects the hollow tube actuator to the hollow tube;
whereby to pass a suture through a surgical site, a user passes a suture through the hollow needle, extending and retracting the hollow tube and pair of jaws to grasp and retrieve the suture.

6. The suture passer of claim 5, further comprising:
a jaw pin slot within the hollow tube;
   the jaw pin free to slide within the jaw pin slot;
   the jaw pin slot defining a range of motion of the pair of jaws with respect to the connecting rod between the pair of jaws open and the pair of jaws closed, but partially exposed to avoid interference with the suture.

7. The suture passer of claim 6, wherein the hollow needle further comprises:
a curved guide;
   the curved guide altering the path of the suture from parallel to the hollow tube, to causing the suture to exit toward the pair of jaws.

8. The suture passer of claim 5, wherein the pair of jaws is formed from:
a primary hinge between the pair of jaws and the connecting rod;
two arms extending from the primary hinge, each arm of the two arms including a secondary hinge; and
a clamping tip formed by tips of the two arms.

9. A suture passer device comprising:
a hollow needle for passing a suture through an incision;
a suture retriever parallel to the hollow needle;
   the suture retriever including a connecting rod sliding within a hollow tube;
   a set of jaws attached to a distal end of the connecting rod via a hinge;
   the hollow tube able to partially surround the set of jaws;
      the jaws in a closed position when partially enclosed by the hollow tube;
      the jaws in an open position when free of the hollow tube;
a jaw actuator;
   inward and outward motion of the jaw actuator moving the connecting rod toward and away from a body;
a hollow tube actuator;
   inward and outward motion of the hollow tube actuator moving the hollow tube toward and away from the body;
a jaw pin that connects the jaw actuator to the connecting rod; and
a tube pin that connects the hollow tube actuator to the hollow tube;

whereby the hollow needle passes a suture within the path of the set of jaws, the set of jaws used to grip and retrieve the suture.

10. The suture passer of claim 9, further comprising:
a jaw pin slot within the hollow tube;
the jaw pin free to slide within the jaw pin slot;
the jaw pin slot defining a range of motion of the set of jaws with respect to the connecting rod, the limits of the range of motion including the set of jaws open, and the set of jaws closed but partially exposed to avoid interference with a captured suture.

11. The suture passer of claim 9, wherein the set of jaws is formed from:
a primary hinge between the set of jaws and the connecting rod;
two arms extending from the primary hinge, each arm of the two arms including a secondary hinge; and
a clamping tip formed by tips of the two arms.

* * * * *